(12) United States Patent
Averheim et al.

(10) Patent No.: US 11,492,752 B2
(45) Date of Patent: Nov. 8, 2022

(54) METHOD AND DEVICE FOR TREATING BIOMASS

(71) Applicant: VALMET AB, Sundsvall (SE)

(72) Inventors: Andreas Averheim, Sundsvall (SE); Francois Lambert, Sundsvall (SE)

(73) Assignee: VALMET AB, Sundsvall (SE)

( * ) Notice: Subject to any disclaimer, the term of this patent is extended or adjusted under 35 U.S.C. 154(b) by 210 days.

(21) Appl. No.: 16/605,146

(22) PCT Filed: May 2, 2018

(86) PCT No.: PCT/EP2018/061132
§ 371 (c)(1),
(2) Date: Oct. 14, 2019

(87) PCT Pub. No.: WO2018/202673
PCT Pub. Date: Nov. 8, 2018

(65) Prior Publication Data
US 2021/0140105 A1 May 13, 2021

(30) Foreign Application Priority Data
May 2, 2017 (EP) .................................. 17169000

(51) Int. Cl.
D21B 1/36 (2006.01)
C12M 1/00 (2006.01)
D21C 1/04 (2006.01)
D21C 1/10 (2006.01)
D21C 5/00 (2006.01)

(52) U.S. Cl.
CPC ............... *D21B 1/36* (2013.01); *C12M 45/06* (2013.01); *C12M 45/09* (2013.01); *C12M 45/20* (2013.01); *D21C 1/04* (2013.01); *D21C 1/10* (2013.01); *D21C 5/005* (2013.01)

(58) Field of Classification Search
CPC ..................................... D21C 1/02; D21C 1/04
See application file for complete search history.

(56) References Cited

U.S. PATENT DOCUMENTS 5,198,074 A * 3/1993 Villavicencio ............ C12P 7/08
127/37
5,338,366 A 8/1994 Grace et al.
(Continued)

OTHER PUBLICATIONS

Extended European Search Report in EP Application No. 17169000. 1, dated Oct. 5, 2017 (9 pages).
(Continued)

*Primary Examiner* — Anthony Calandra
(74) *Attorney, Agent, or Firm* — Foley & Lardner LLP

(57) ABSTRACT

The invention relates to a method for treating biomass (2). Biomass (2) is fed to a pressurized prehydrolysis reactor unit (8) by means of a feeding system (5, 7), wherein by means of the feeding system (5, 7) the biomass (2) is compressed. A filtrate is squeezed out of the biomass (2) by means of the feeding system (5, 7), in particular by a first plug screw (5) or a second plug screw (7) of the feeding system (5, 7). The biomass (2) is then thermally treated in the pressurized prehydrolysis reactor unit (8), discharged from the pressurized prehydrolysis reactor unit (8) afterwards, diluted with the filtrate before or after the discharge, and treated with an enzyme subsequently.

6 Claims, 1 Drawing Sheet

(56) References Cited

U.S. PATENT DOCUMENTS

| | | |
|---|---|---|
| 2011/0281298 A1 | 11/2011 | Rawls et al. |
| 2013/0029406 A1 | 1/2013 | Dottori et al. |
| 2013/0146049 A1* | 6/2013 | Ottonello ............... D21C 1/00 |
| | | 127/34 |
| 2014/0083939 A1 | 3/2014 | Nguyen et al. |
| 2014/0170723 A1 | 6/2014 | Dobson et al. |
| 2014/0295509 A1 | 10/2014 | Van Der Meulen et al. |
| 2016/0312318 A1* | 10/2016 | Ottonello ............... C08H 8/00 |
| 2020/0157739 A1* | 5/2020 | Toll ....................... D21C 1/02 |

OTHER PUBLICATIONS

International Search Report and Written Opinion in International Application No. PCT/EP2018/061132, dated Jul. 3, 2018 (16 pages).

* cited by examiner

METHOD AND DEVICE FOR TREATING BIOMASS

This application is a U.S. National Phase Application under 35 U.S.C. § 371 of International Application No. PCT/EP2018/061132, filed on May 2, 2018, which claims the benefit of EP 17169000.1 filed on May 2, 2017, the entire contents of which are incorporated herein by reference in their entireties.

FIELD OF THE INVENTION

The invention generally relates to a treatment of biomass. In particular, the invention relates to a method and a device for treating biomass, wherein the biomass is exposed to a prehydrolysis step first and to a hydrolysis step subsequently.

BACKGROUND OF THE INVENTION

Prehydrolysis with the purpose of dissolving hemicellulose sugars from a lignocellulosic biomass (often called pretreatment if preceding an enzymatic hydrolysis stage) are known. They are in many cases conducted with acid as a catalyst at temperatures above 100° C. in a pressurized steam environment in a reactor, typically between approximately 150 to 225° C. with residence times ranging from approximately 1 to 120 minutes. The acid can be provided externally to the biomass upstream of the reactor in an impregnation stage (dilute acid hydrolysis). Alternatively, the acid can be created within the reactor through formation of acetic acid due to hydrolysis of hemicellulose upon heating the biomass (autohydrolysis). A hybrid between the two processes has also been suggested, according to which acetic acid is being removed from the product discharged from the reactor and is being recirculated back to an impregnation step preceding the reactor in a kind of reinforced autohydrolysis.

SUMMARY OF THE INVENTION

It is an object of the present invention to provide an improved process for treating biomass.

This object is achieved by the subject-matter of the independent claims. Further exemplary embodiments are evident from the dependent claims and the following description.

According to a first aspect of the invention a method for treating biomass is provided. In one step of the method, biomass is fed to a pressurized prehydrolysis reactor unit by means of a feeding system, wherein by means of the feeding system the biomass is compressed, and—in parallel—a filtrate is squeezed out of the biomass by means of the feeding system. For example, biomass that has been moisturized by e.g. being soaked in water before, can be dewatered by the compression of the feeding system. By this, the filtrate is separated from the rest of the biomass. The filtrate can be a residual plug screw pressate. The pressate can contain biomass, inorganic substances such as ash, and water soluble organic substances originating from the biomass. In particular, a part of the inorganic substances can be removed from the biomass by the feeding system as suspended or dissolved solids in the plug screw pressate.

The biomass—without the squeezed out and, thus, separated filtrate—is thermally treated in the pressurized prehydrolysis reactor unit. Said thermal treatment can particularly include heating the biomass and pressurizing the biomass with steam. Afterwards, the thermally treated biomass is discharged from the pressurized prehydrolysis reactor unit.

The biomass is diluted with the filtrate either before or after being discharged from the pressurized prehydrolysis reactor unit.

Subsequently, the discharged and diluted biomass is treated with an enzyme.

For example, straw can be used as biomass and can be moisturized before entering the reactor, either with a dilute solution containing external catalyst (dilute acid hydrolysis), a recirculated catalyst (reinforced autohydrolysis) or water (autohydrolysis). Also, acetic acid can be recirculated and can be mixed with the steam going to the reactor unit in an organosolv process. Also in this case, the biomass can be moisturized before entering the reactor unit. The moisturizing or the combined moisturizing and acid charge can take place in a mixer screw, a mixing zone, an impregnation reactor or a soaking reactor. The biomass can also be moisturized in a biomass washing and cleaning stage.

A lignocellulosic biomass can be used in the method and in the device according to the present invention. The biomass can be based on agricultural residues and energy crops, which are commonly proposed as source for so called "2G bioethanol" and "green renewable chemicals". However, they usually contain high quantities of ash (inorganic substances). Some of the inorganics originate from the handling of the material for example sand, soil and stones which are collected with the biomass, but a large part of the inorganics is embedded in the biomass itself. If exposed to acid, some of the inorganics consume the acid through buffering reactions.

As mentioned above, a dilute acid hydrolysis can be applied to the biomass, which purpose is to acidify the biomass before entering the prehydrolysis reactor. However, when applying such a method, buffering reactions might consume up to 20 kg sulfuric acid per ton of biomass. This acid is not recoverable, meaning that the presence of inorganics increases the necessary acid charge in order to reach a desired acid catalyst concentration in the prehydrolysis reactor. Squeezing out the filtrate out of the biomass before feeding it to the pressurized prehydrolysis reactor enables to separate unwanted, acid consuming substances, in particular inorganic substances such as ash, from the biomass, which is to be fed to the pressurized prehydrolysis reactor. As a result, the acid consumption particularly in an impregnation step prior to the thermal treatment in the pressurized prehydrolysis reactor unit can be decreased.

Furthermore, an autohydrolysis can be applied, which can lead to a presence of buffering inorganics in the prehydrolysis reactor, wherein the buffering inorganics slow down the process, if they consume acid created in the autocatalytic reactions. It is also possible that the process becomes less selective, if the catalyst concentration is very low in the prehydrolysis reactor, which could decrease the process yield and increase the rate of formation of unwanted byproducts. Squeezing out the filtrate out of the biomass before feeding it to the pressurized prehydrolysis reactor enables to separate unwanted acid buffering substances, in particular inorganic substances such as ash, from the biomass, which is fed to the pressurized prehydrolysis reactor unit. As a result, an acid consumption of acid buffering inorganics within the prehydrolysis reactor unit can be reduced, and the catalyst concentration within the prehydrolysis reactor unit can be increased. This helps preventing that the process becomes less selective, that the process yield decreases, that the rate of formation of unwanted byproducts increases and that the prehydrolysis process slows down. Thus, a required residence time of the biomass within the impregnation reaction unit can be reduced.

For compressing the biomass and for squeezing the filtrate out of the biomass, the feeding system can comprise at least one plug screw. The plug screw may also be defined as plug screw feeder. In particular, the plug screw may be a part of the plug screw feeder. The plug screw can be a conveyor means which, by rotating around an axis, conveys the biomass into the reactor unit. By means of the plug screw, it is possible to generate a plug of biomass at an inlet of the reactor unit.

The compression is advantageous because the biomass, as it is delivered by a supplier for example, can be a very bulky material. This is especially the case if non-wood material is used. This bulky material can be compressed such that a plug of biomass is generated before entering the reactor unit. In the plug screw, a volumetric compression of the biomass occurs due to the geometry of the screw. However, a compression can also occur in a plug pipe which can be adapted for transferring the material, in particular the biomass to the reactor. The compression in such a plug pipe can be due to friction and to a pressure applied by a retaining member, e.g. a blow back damper, as will be described hereinafter. The plug pipe may be a portion of the plug screw feeder located downstream of the plug screw, i.e. the plug pipe may be the end of the volumetric compression area in which the volumetric compression of the biomass is carried out.

The feeding of the biomass into the reactor unit can be interrupted by means of a retaining member, that is arranged upstream of the reactor unit. For example, the retaining member is arranged at the bottom part of the reactor unit or at the inlet of the reactor unit. For example, the retaining member is designed as a damper or sealing member which is arranged between the feeding part and the reactor unit. The retaining member may be a part of the reactor unit which is arranged at the bottom part of the reactor unit. The retaining member may be a blow back damper. For example, the retaining member is located between the reactor unit and the plug screw of the feeding part. A damper may be used in order to increase the density of the material, e.g. the biomass, which comes from the plug screw as well as to close the feeding inlet into the reactor unit, for example if no material is to be fed into the reactor unit. The damper may also be used to break the plug and to allow the material, e.g. the biomass, to expand in the reactor unit.

According to an embodiment of the invention, a pre-compression of the biomass is conducted by means of a force-feed screw before feeding the biomass into the reactor. In this case, the material is pre-compressed by the force feed screw before it is compressed by the feeding system, in particular the plug screw, during the compression step. In other words, the biomass may first be pre-compressed by the force feed screw, then compressed by the feeding system, in particular the plug screw, and then fed into the reactor for impregnation.

In general, when using bulky material, it is beneficial to use a force-feed screw to feed the plug screw and afterwards the reactor unit in order to increase the compression and to generate a more compacted plug. In particular, a force-feed screw for pre-compressing may be advantageous if the biomass is a non-wood material. However, it is not necessary to use a force-feed screw, especially if the biomass is a high-density material, such as wood. A force-feed screw may also support the feeding of the reactor unit with the respective biomass. It should be mentioned that the force-feed screw may be integrated into the feeding step of the reactor unit in addition to the plug screw. For example, if bulky material is used, it is advantageous to use the pre-compression step with the force feed screw before the material is compressed by the plug screw in the compression step. Both pre-compression and compression may thus be combined before feeding the compressed biomass into the reactor unit. If no bulky material is used the pre-compression step can be omitted.

The biomass can be fed into and treated in more than one reactor unit. If the biomass is treated in more than one reactor, e.g. in an impregnation reactor and in a prehydrolysis reactor, this treatment is done in series. For example, biomass can be fed into the impregnation reactor unit in particular by means of a first plug screw, and then be impregnated in the impregnation reactor unit. Afterwards, the biomass can be fed out of the impregnation reactor unit to the subsequent respectively downstream prehydrolysis reactor unit in particular by means of a second plug screw. The biomass can also be treated in two or more prehydrolysis reactors in series at same or different temperature and pressure.

According to an embodiment, the thermally treated biomass is discharged from the pressurized prehydrolysis reactor through a steam explosion. The steam explosion could be defined as a rapid pressure decrease leading to a flashing of the steam. In particular, the biomass can be exposed to steam within the prehydrolysis reactor unit, wherein the steam is fed into the prehydrolysis reactor unit in addition to the biomass. By exposing the biomass to steam, the biomass is pressurized in the prehydrolysis reactor unit, and by heating the pressurized biomass, the thermally treated biomass is generated. This thermally treated biomass is discharged from the prehydrolysis reactor unit afterwards, wherein a steam explosion on the thermally treated biomass may take place during the discharge of the thermally treated biomass, for example in a blow valve arranged downstream the prehydrolysis reactor unit. A restriction which may have the shape of a hole through which the thermally treated biomass is discharged may provide a means in which the steam explosion occurs. In particular, this restriction makes it possible that the steam can expand such that a flashing may occur.

In the context of the present invention, a steam explosion may be understood as a violent boiling or a flashing of water into steam. Therefore, steam is introduced into the prehydrolysis reactor unit such that the steam may act on the biomass within the prehydrolysis reactor unit. Excess steam may be recovered after discharging the biomass from the prehydrolysis reactor unit, i.e. after the steam explosion in the prehydrolysis reactor unit. This steam may be recirculated to other steps in the treatment process. After the steam treatment of the biomass has been carried out, the steamed biomass may be discharged from the prehydrolysis reactor unit, wherein a steam explosion of the treated biomass takes place. In particular, the steam explosion occurs when discharging the treated biomass out of the prehydrolysis reactor unit. After the steam explosion on the treated biomass has been carried out, the steamed and/or steam exploded biomass may be subjected to further treatment steps after the reactor unit.

According to another embodiment, the thermally treated biomass is diluted before it is discharged from the pressurized prehydrolysis reactor unit. In particular, the thermally treated biomass is diluted in a downstream part of the pressurized prehydrolysis reactor, e.g. between the pressurized prehydrolysis reactor unit and a neutralization unit, where the enzyme treatment is applied. The diluted biomass can be discharged e.g. through an orifice and/or a blow valve of the pressurized prehydrolysis reactor unit.

While being discharged, the temperature of the biomass can be between 45 and 130° C. In particular, the biomass can have a temperature below 100° C. during discharging and no flashing occurs during discharging. Alternatively, the biomass can have a temperature above 100° C. during discharging and a flashing occurs. However, this flashing occurs without a steam explosion occurring during discharging.

Furthermore, the diluted biomass can be dewatered after being discharged from the pressurized prehydrolysis reactor unit and before being treated with the enzyme. For example, the material can be dewatered in a screw press or other dewatering machine after being discharged.

According to a further embodiment, the method further comprises the step of impregnating the biomass with a reactant in an impregnation reactor unit prior to feeding the impregnated biomass to the pressurized prehydrolysis reactor unit. The impregnation reactor unit is partially filled with a reactant, such that a reaction between the fed biomass and the reactant takes place in order to obtain an impregnated biomass.

In particular, the reactant can be water, acid or a catalyst. The reactant, which may be a catalyst, can be evenly distributed in the biomass when it is added into the reactor unit. Residual reactant from the impregnated biomass can be removed in a further processing step following the discharge of the impregnated biomass out of the reactor unit. The residual reactant can be supplied into a recirculation circuit. The reactant to be filled into the reactor unit can be provided from the recirculation circuit and/or from a reservoir. Using a recirculation circuit provides the advantage that reactant which has already been used to impregnate the biomass and which afterwards was separated from the impregnated biomass, can again be used for impregnation in the reactor unit. A further processing step may for instance be a dewatering stage, a hydrolysis stage, or another treatment process following the discharge of the impregnated biomass from the impregnation reactor unit. As an alternative or in addition to the usage of a recirculation circuit, a reservoir from which the reactant can be filled into the impregnation reactor unit can be provided. The amount of reactant which can be supplied from the reservoir can be regulated depending on the amount of reactant which can be supplied by the recirculation circuit. In this manner, it may be possible that a constant fill level within the impregnation reactor unit can be achieved.

The reactant may be a fluid, e.g. water, preferably a liquid comprising chemicals, e.g. an aqueous solution. According to an embodiment of the invention, the reactant is a liquid comprising chemicals selected from the group consisting of an acid, a catalyst or mixtures thereof. For example, the liquid is an aqueous solution, EtOH or mixtures thereof. The chemicals are selected from the group consisting of a catalyst, an acid, a mineral acid preferably $H_2SO_4$, organic acid preferably acetic acid, nitric acid, phosphoric acid, or mixtures thereof. $H_2SO_4$ is the preferred chemical. Liquid containing acetic acid, for example from the recirculated stream, is also a preferred chemical.

In the context of the present invention, the term "reactant" is to be understood as a liquid comprising chemicals, wherein the liquid may be an aqueous solution, EtOH or a similar mixture and the chemicals may comprise a catalyst, an acid like $H_2SO_4$ or acetic acid or similar mixtures. The liquid may comprise water or another solvent.

Alternatively, a mixture of water and solvent is possible. The reactant may also be a filtrate obtained from another part of the process, for example from following or previous steps of the impregnation in the reactor unit. The reactant may be derived from a recirculation of filtrates, liquids or pressates which are obtained at different positions in the process. This may, for example, be a condensate or partial condensate of a steam explosion flash vapor, a byproduct from evaporation, a distillation of fermented slurry, or a filtrate from a dewatering stage.

The recirculated liquid reactant may be treated, e.g. fractionated into several fractions. For example, solid fractions may be removed from the recirculated stream or a chemical may be removed from the recirculated stream. A screen filtration may for instance be conducted. The reactant may be a liquid, e.g. an aqueous solution, comprising chemicals, such as acid. For example, the reactant may comprise a nitric acid, a phosphoric acid or a sulfuric acid. The temperature of the liquid should be between 45 and 99° C., 60 to 90° C., 70 to 90° C., 60 to 80° C., 105 to 140° C., 110 to 135° C., or 120 to 150° C. The pressure during the impregnation may for instance be set between atmospheric pressure and 2, 4, or 5 bars. The preferred pressure during impregnation is atmospheric pressure.

It is possible that different concentrations of chemicals are present in the liquid. An acid may for instance be $H_2SO_4$, acetic acid, nitric acid, phosphoric acid, oxalic acid, $SO_2$, lactic acid, or alkali. A possible alkali is for instance NaOH, $Na_2CO_3$ or $K_2CO_3$. A solvent like EtOH as well as a mixture of the above mentioned chemicals is possible. The amount of acid used may be controlled by the pH-value of the liquid fed into the reactor unit or the pH-value of the liquid present within the reactor unit or the pH-value of the liquid contained in the material which is discharged from the reactor unit, for example in a dewatering zone within the reactor unit. A typical sulfuric acid concentration of the reactant to be filled into the reactor unit is between 0.05% and 4% for wood material, and also between 0.05% and 4% for non-wood material. The concentration of the reactant is dependent on the desired product and on the requirements of the impregnated biomass in the further processing steps. If the reactant is added to the biomass at different positions, the concentrations of the reactant at each position may be different. A typical acid makeup may be between 5 and 60 kg per ton, depending on the raw material, on the flow of the total and recirculated liquid reactant in the reactor unit, on the liquid reactant flow in general and on the target for a pH-value or an acid concentration.

According to another embodiment, the biomass is fed to the impregnation reactor unit, in particular to an upstream part of the impregnation reactor unit, by means of a first plug screw of the feeding system, wherein the impregnation reactor unit is partly filled with the reactant, and wherein the filtrate is squeezed out of the biomass by means of the first plug screw while the biomass is fed to the impregnation reactor unit, in particular to the upstream part of the impregnation reactor unit, by means of the first plug screw. This embodiment can be applied in particular in a dilute acid hydrolysis process, wherein the filtrate can be separated from the rest of the biomass prior to feeding the biomass to the impregnation reactor unit. For example, the impregnation reactor unit may be fed with dry straw by means of the first plug screw of the feeding system. A simple mixing step can be added prior to the feeding, wherein some water and possibly steam may be provided to the biomass upstream of the first plug screw. These combined mixing and squeezing steps enable removal of some of the inorganics before entering the impregnation reactor unit, thus decreasing the acid consumption in the impregnation stage.

According to another embodiment, the filtrate is squeezed out of the impregnated biomass by means of a second plug screw of the feeding system while the impregnated biomass is fed to the pressurized prehydrolysis reactor unit by means of the second plug screw. This embodiment can be applied in particular in an autohydrolysis process, wherein the filtrate can be separated from the rest of the biomass prior to feeding the biomass to the pressurized prehydrolysis reactor unit. For example, an impregnation reactor unit can be arranged upstream of the pressurized prehydrolysis reactor unit. The impregnation reactor unit can be used simply to soak the biomass with water (preceding the autohydrolysis). In such a case, it is likely that the filtrate or pressate needs to be recirculated back to the impregnation reactor unit. A part of the recirculating filtrate or pressate, in particular the inorganics, can be removed from the recirculation loop by squeezing it out. This helps to increase the efficiency of the autohydrolysis reaction.

In cases, where a prehydrolysis or pretreatment process is followed by an enzymatic hydrolysis stage with the purpose of converting particularly cellulose, and yet unreacted hemicellulose into monomeric sugars, it is necessary to increase and stabilize the pH value of the biomass slurry discharged from the prehydrolysis reactor from approximately 0.5-4 up to around the suitable pH interval for enzyme stage, for example around pH 5, alternatively between 4.75 and 5.25 or 4.7 and 5.3. In most cases a dilution of the biomass slurry is also necessary in order to be able to mix, knead or agitate the slurry with the enzymes. The dilute acid hydrolysis and the autohydrolysis both create a filtrate respectively a residual plug screw pressate which can contain biomass, inorganic substances such as ash, and water soluble organic substances originating from the biomass.

According to the present invention the thermally treated biomass is diluted with the filtrate before or after being discharged from the pressurized prehydrolysis reactor unit.

Thus, according to one embodiment of the invention, the method further comprises the step of diluting the discharged biomass with the filtrate. In other words, the present application proposes that the biomass, which has been thermally treated in the pressurized prehydrolysis reactor unit and which has been discharged from the pressurized prehydrolysis reactor unit, is diluted with the filtrate and treated with an enzyme. The filtrate respectively pressate supports an increase of the pH value up to 5 with less use of external chemicals, such as alkali, and also helps to stabilize the pH value around the suitable pH interval for enzyme stage, for example around pH 5, alternatively between 4.75 and 5.25 or 4.7 and 5.3 through buffering reactions during the enzymatic hydrolysis. Basic technologies such as screening, filtration or sedimentation can be applied before using the pressate for dilution in order to separate biomass to be sent back to prehydrolysis, or to separate sand and stones to be removed from the process.

According to another embodiment of the invention, the method further comprises the step of diluting the thermally treated biomass with the filtrate before the thermally treated biomass is discharged from the pressurized prehydrolysis reactor unit. In other words, the present application proposes that the biomass, which has been thermally treated in the pressurized prehydrolysis reactor unit is diluted with the filtrate before it is discharged and treated with an enzyme. The filtrate respectively pressate supports an increase of the pH value up to around the suitable pH interval for enzyme stage, for example around pH 5, alternatively between 4.75 and 5.25 or 4.7 and 5.3 with less use of external chemicals, such as alkali, and also helps to stabilize the pH value around the suitable pH interval for enzyme stage, for example around the suitable pH interval for enzyme stage, for example around pH 5, alternatively between 4.75 and 5.25 or 4.7 and 5.3, through buffering reactions during the enzymatic hydrolysis. Basic technologies such as screening, filtration or sedimentation can be applied before using the pressate for dilution in order to separate biomass to be sent back to prehydrolysis, or to separate sand and stones to be removed from the process.

According to another embodiment of the method, the discharged biomass is diluted with the filtrate before the discharged biomass is treated with the enzyme. Alternatively or additionally the discharged biomass is diluted with the filtrate while the discharged biomass is treated with the enzyme.

According to another aspect of the invention, a device for treating biomass is provided. The device comprises a feeding system, a pressurized prehydrolysis reactor unit for thermally treating the biomass and for discharging the thermally treated biomass and a neutralization unit. The feeding system is adapted for compressing and feeding the biomass into the pressurized prehydrolysis reactor unit and for squeezing out a filtrate out of the biomass. Furthermore, the neutralization unit is adapted for treating the discharged biomass with an enzyme to increase a pH value of the discharged biomass.

According to an embodiment the device further comprises an impregnation reactor unit for impregnating the biomass with a reactant. A first plug screw of the feeding system is adapted for compressing and feeding the biomass into the impregnation reactor unit. A second plug screw of the feeding system is adapted for compressing and feeding the impregnated biomass into the pressurized prehydrolysis reactor unit. The first plug screw and/or the second plug screw are adapted for squeezing out a filtrate out of the biomass. For example, the first plug screw can be adapted for squeezing out a filtrate out of the biomass, if a dilute acid hydrolysis process is applied using the device, and the first plug screw can be adapted for squeezing out a filtrate out of the biomass, if a autohydrolysis process is applied using the device. Furthermore, the device is adapted for diluting the discharged biomass with the squeezed out filtrate.

The device according to the second aspect serves to execute a method as per the first aspect of the invention. Thus, to avoid repetitions, regarding technical effects, advantages and embodiments of the device according to the second aspect of the invention, it is referred to the above explanations in context with the method according to the first aspect of the invention and to the exemplary embodiments of the invention as shown by the drawings and as described in the following.

DETAILED DESCRIPTION OF THE DRAWINGS

Figure 1:
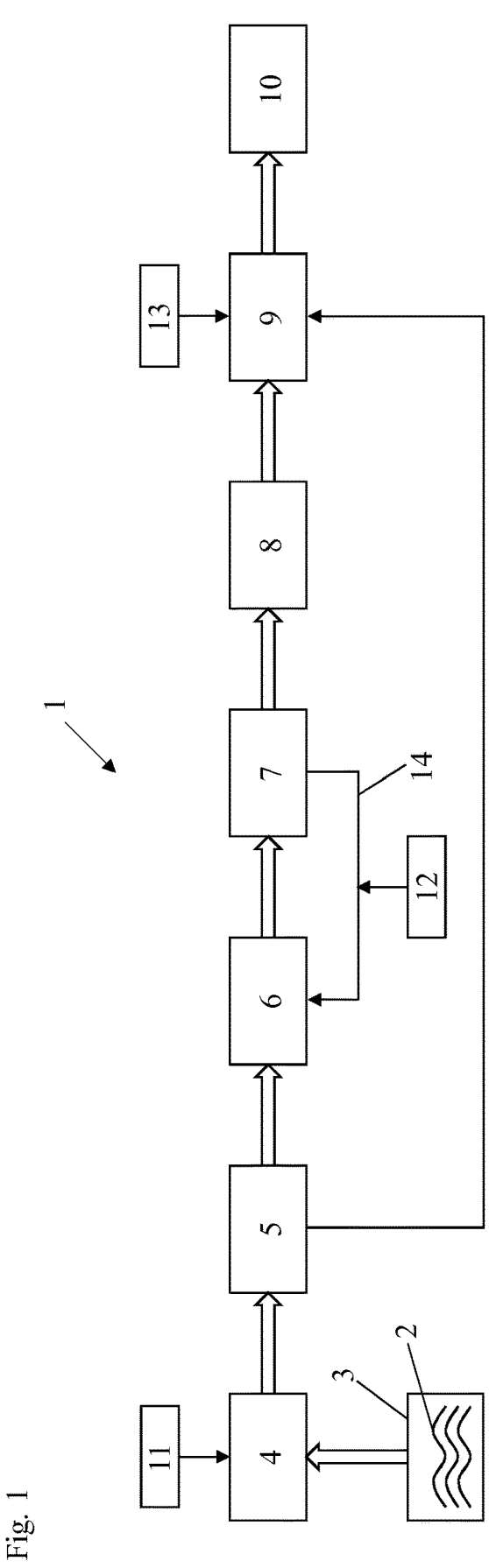
FIG. 1 shows a schematic plan of a first device for executing a method for treating biomass according to a first embodiment of the invention and FIG. 2 shows a schematic plan of a second device for executing a method for treating biomass according to a second embodiment of the invention.

FIG. 1 shows a device 1 for treating biomass 2, e.g. dry straw, which is stored within a biomass reservoir 3. In particular, FIG. 1 shows how a dilute acid hydrolysis process can be applied to the biomass 2. The device 1 comprises a mixing unit 4, a first plug screw 5, an impregnation reactor unit 6, a second plug screw 7, a pressurized prehydrolysis reactor 8, a neutralization unit 9, an enzymatic hydrolysis reactor unit 10, a water reservoir 11, an acid reservoir 12 and an alkali reservoir 13.

The biomass 2 is fed to the mixing unit 4, e.g. by means of a feeding unit (not shown). Water stored within the water reservoir 11 is also fed to the mixing unit 4, e.g. by pumping means and a conduit (both not shown). Furthermore, steam can be fed to the mixing unit, optionally (not shown). The biomass 2 is mixed with the water and, if provided, with the steam within the mixing unit 4.

The first plug screw 5 and the second plug screw 7 are both elements of a feeding system of the device 1. The first plug screw 5 of the feeding system compresses and feeds mixed biomass 2 (which is moistured as a result of the previous mixing with water and with steam, optionally) from the mixing unit 4 into the impregnation reactor unit 6. The mixed biomass 2 is impregnated with a reactant in form of acid in the impregnation reactor unit 6. In the shown example, the acid reservoir 12 can be connected to the impregnation reactor unit 6, such that acid or acid and water stored within the acid reservoir 12 is fed to the impregnation reactor unit 6, and the impregnation reactor unit 6 is partly filled with the acid, which impregnates the mixed biomass 2.

The biomass 2 can contain high quantities of ash (inorganic substances). Some of the inorganics originate from the handling of the material for example sand, soil and stones which are collected with the biomass, but a large part of the inorganics is embedded in the biomass itself. If exposed to acid, the inorganics consume the acid through buffering reactions.

By means of the first plug screw 5 a filtrate respectively a pressate (not shown) is squeezed out of the mixed biomass 2 while the mixed biomass 2 is fed to the impregnation reactor unit 6 by means of the first plug screw 5. Before entering the impregnation reactor unit 6, the filtrate is separated from the mixed biomass 2, which is fed by the first plug screw 2 to the impregnation reactor unit 6. The filtrate is not fed to the impregnation reactor unit 6. Instead, the filtrate is fed to the neutralization unit 9. The filtrate can be a residual plug screw pressate. The pressate can contain biomass, inorganic substances such as ash, and water soluble organic substances originating from the biomass. The squeezing of the mixed biomass 2 enables to remove some of the inorganics before entering the impregnation reactor unit 6, thus decreasing an acid consumption of inorganics such as ash within the impregnation reactor unit 6.

Residual acid from the impregnated biomass 2 can be removed in a further processing step following the discharge of the impregnated biomass out of the impregnation reactor unit 6. The residual acid can be supplied into a recirculation circuit 14. Water can be added in the recirculation loop 14, or directly in the impregnation unit 6 or in the acid reservoir 12. Thus, acid to be filled into the impregnation reactor unit 6 can be provided from the recirculation circuit 14 and/or from the acid reservoir 12.

The second plug screw 7 of the feeding system compresses and feeds impregnated biomass 2 from the impregnation reactor unit 6 into the pressurized prehydrolysis reactor unit 8. During the feeding, the impregnated biomass 2 can also be dewatered by means of the second plug screw 7. Within the pressurized prehydrolysis reactor unit 8 the impregnated biomass 2 is thermally treated, i.e. heated and pressurized with steam for a certain time. The heating can e.g. be done with heating means (not shown) of the pressurized prehydrolysis reactor unit 8, and the pressurizing can e.g. be done with steam generation means (not shown) of the pressurized prehydrolysis reactor unit 8.

The thermally treated biomass 2 can be discharged from the pressurized prehydrolysis reactor 8 through a steam explosion. Alternatively, the thermally treated biomass 2 can be diluted before it is discharged from the pressurized prehydrolysis reactor unit. In the latter case, the biomass 2 can either have a temperature below 100° C. during discharging, wherein no flashing occurs during discharging, or the biomass can have a temperature above 100° C. during discharging and a flashing without a steam explosion occurs during discharging. Generally, while being discharged, a temperature of the diluted biomass 2 can be between 45 and 130° C. Furthermore, the biomass 2 can be dewatered after being discharged from the pressurized prehydrolysis reactor 8 unit.

After being discharged from the prehydrolysis reaction unit 8 the biomass 2 can have a pH value in a range from 0.5 to 4. In the hydrolysis reactor unit 10 an enzymatic hydrolysis process is applied to the biomass 2, wherein cellulose and yet unreacted hemicellulose is converted into monomeric sugars. For this enzymatic hydrolysis process it is necessary to increase the pH value of the biomass 2 up to a value of around the suitable pH interval for enzyme stage, for example around pH 5, alternatively between 4.75 and 5.25 or 4.7 and 5.3 and to stabilize the pH value at this level. To achieve this, the discharged biomass 2 is treated with an enzyme, in the shown example alkali, for increasing and stabilizing the pH value of the discharged biomass 2. This treatment is done within the neutralization unit 9, wherein alkali contained within the alkali reservoir 13 can be fed from the alkali reservoir 13 to the neutralization unit 9 by respective feeding means (not shown).

Furthermore, the filtrate, which has been squeezed out from the mixed biomass before, is fed to the neutralization unit 9, e.g. by conveying means and a conduit (both not shown). By this, the discharged biomass 2 can be diluted with the filtrate. In other words, the biomass 2, which has been discharged from the pressurized prehydrolysis reactor unit 8, is diluted with the filtrate and treated with an enzyme. The filtrate supports an increase of the pH value up to around the suitable pH interval for enzyme stage, for example around pH 5, alternatively between 4.75 and 5.25 or 4.7 and 5.3 with less use of external alkali, and also helps to stabilize the pH value around 5 through buffering reactions during the enzymatic hydrolysis. Consequently, a lower amount of alkali from the alkali reservoir 13 is needed to stabilize the pH value in the neutralization unit 9. In the shown example, the discharged biomass 2 is diluted with the filtrate while the discharged biomass 2 is treated with the enzyme in the neutralization unit 9. Alternatively or additionally, the discharged biomass 2 can also be diluted with the filtrate before the discharged biomass 2 is treated with the enzyme, for example, if the discharged biomass 2 is diluted by the filtrate upstream of the neutralization unit 9. After being treated in the neutralization unit 9, the biomass (now with a pH value of around the suitable pH interval for enzyme stage, for example around pH 5, alternatively between 4.75 and 5.25 or 4.7 and 5.3) can be fed to the hydrolysis reactor unit 10 for being exposed to an enzymatic hydrolysis process as described above. Alternatively, the biomass 2 can be diluted with filtrate in the downstream part of reactor 8 before being discharged.

Figure 2:
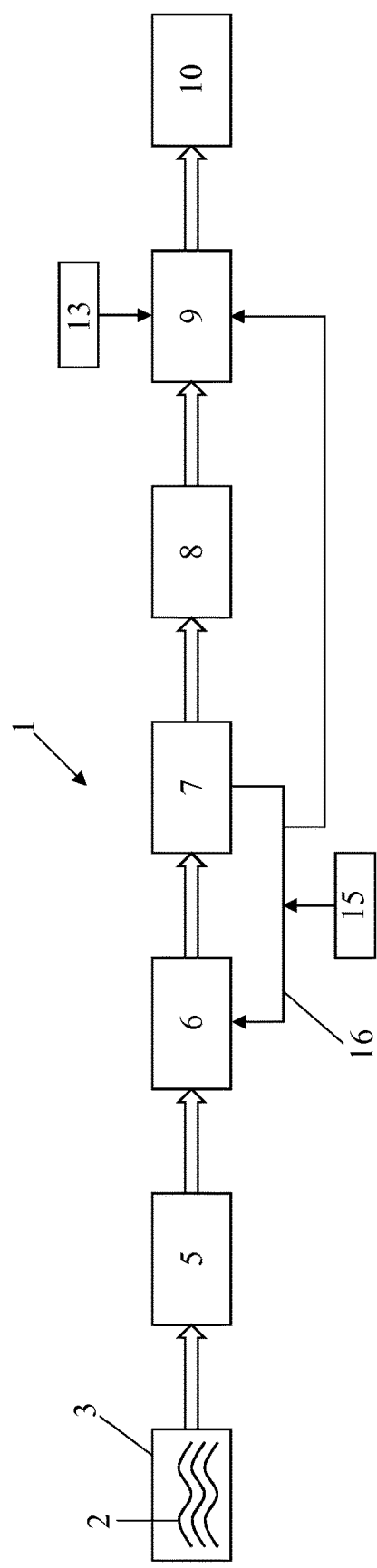

FIG. 2 shows a device 1 for treating biomass 2, e.g. dry straw, which is stored within a biomass reservoir 3. In particular, FIG. 2 shows how an autohydrolysis process can be applied to the biomass 2. The device 1 comprises a first plug screw 5, an impregnation reactor unit 6, a second plug screw 7, a pressurized prehydrolysis reactor 8, a neutralization unit 9, an enzymatic hydrolysis reactor unit 10, an alkali reservoir 13 and a water reservoir 15.

The first plug screw 5 and the second plug screw 7 are both elements of a feeding system of the device 1. The first plug screw 5 of the feeding system compresses and feeds biomass 2 from the biomass reservoir 3 into the impregnation reactor unit 6. The biomass 2 is impregnated with a reactant in the impregnation reactor unit 6. In particular, the biomass is soaked with water in the impregnation reactor unit 6. In the shown example, the water reservoir 15 can be connected to the impregnation reactor unit 6, such that water stored within the water reservoir 15 is fed to the impregnation reactor unit 6, and the impregnation reactor unit 6 is partly filled with the water, which impregnates the biomass 2.

The biomass 2 can contain high quantities of ash (inorganic substances). Some of the inorganics originate from the handling of the material for example sand, soil and stones which are collected with the biomass, but a large part of the inorganics is embedded in the biomass itself. If exposed to acid, the inorganics consume the acid through buffering reactions.

By means of the second plug screw 7 a filtrate respectively a pressate (not shown) is squeezed out of the biomass 2 while the biomass 2 is fed to the prehydrolysis reactor unit 8 by means of the second plug screw 7. Before entering the prehydrolysis reactor unit 8, the filtrate is separated from the biomass 2, which is fed by the second plug screw 7 to the prehydrolysis reactor unit 8. The filtrate is not fed to the prehydrolysis reactor unit 8. Instead, the filtrate is fed to a pressate recirculation circuit 16, which leads to the impregnation reactor unit 6 and to the neutralization unit 9. Thus, a first part of the filtrate is fed to the neutralization unit 9 and a second part of the filtrate can be fed to the impregnation reactor unit 6 again (recirculation). The filtrate can be a residual plug screw pressate. The pressate can contain biomass, inorganic substances such as ash, and water soluble organic substances originating from the biomass. The squeezing of the biomass 2 enables to remove some of the inorganics before entering the prehydrolysis reactor unit 8, thus decreasing an acid consumption of inorganics such as ash within the prehydrolysis reactor unit 6.

The second plug screw 7 of the feeding system compresses and feeds impregnated biomass 2 from the impregnation reactor unit 6 into the pressurized prehydrolysis reactor unit 8. During the feeding, the impregnated biomass 2 can also be dewatered by means of the second plug screw 7. Within the pressurized prehydrolysis reactor unit 8 the impregnated biomass is thermally treated, i.e. heated and pressurized with steam for a certain time. The heating can e.g. be done with heating means (not shown) of the pressurized prehydrolysis reactor unit 8, and the pressurizing can e.g. be done with steam generation means (not shown) of the pressurized prehydrolysis reactor unit 8. By this heat treatment within the pressurized prehydrolysis reactor unit 8, acetic acid is liberated from hemicellulose of the biomass 2 (autohydrolysis).

The thermally treated biomass 2 can be discharged from the pressurized prehydrolysis reactor 8 through a steam explosion. Alternatively, the thermally treated biomass 2 can be diluted before it is discharged from the pressurized prehydrolysis reactor unit. In this case, the biomass 2 can either have a temperature below 100° C. during discharging, wherein no flashing occurs during discharging, or the biomass can have a temperature above 100° C. during discharging and a flashing without a steam explosion occurs during discharging. While being discharged, a temperature of the diluted biomass 2 can be between 45 and 130° C. Furthermore, the biomass 2 can be dewatered after being discharged from the pressurized prehydrolysis reactor 8 unit.

After being discharged from the prehydrolysis reaction unit 8 the biomass 2 can have a pH value in a range from 0.5 to 4. In the hydrolysis reactor unit 10 an enzymatic hydrolysis process is applied to the biomass 2, wherein cellulose and yet unreacted hemicellulose is converted into monomeric sugars. For this enzymatic hydrolysis process it is necessary to increase the pH value of the biomass 2 up to a value of around the suitable pH interval for enzyme stage, for example around pH 5, alternatively between 4.75 and 5.25 or 4.7 and 5.3 and to stabilize the pH value at this level. To achieve this, the discharged biomass 2 is treated with an enzyme, in the shown example alkali, for increasing and stabilizing the pH value of the discharged biomass 2. This treatment is done within the neutralization unit 9, wherein alkali contained within the alkali reservoir 13 can be fed from the alkali reservoir 13 to the neutralization unit 9 by respective feeding means (not shown).

Furthermore, the filtrate, which has been squeezed out from the biomass 2 before, is fed to the neutralization unit 12, e.g. by conveying means and a conduit (both not shown). By this, the discharged biomass 2 can be diluted with the filtrate. In other words, the biomass 12, which has been discharged from the pressurized prehydrolysis reactor unit 8, is diluted with the filtrate and treated with an enzyme. The filtrate supports an increase of the pH value up to around the suitable pH interval for enzyme stage, for example around pH 5, alternatively between 4.75 and 5.25 or 4.7 and 5.3 with less use of external alkali, and also helps to stabilize the pH value around the suitable pH interval for enzyme stage, for example around pH 5, alternatively between 4.75 and 5.25 or 4.7 and 5.3 through buffering reactions during the enzymatic hydrolysis. In the shown example, the discharged biomass 2 is diluted with the filtrate while the discharged biomass 2 is treated with the enzyme in the neutralization unit 9.

Alternatively or additionally, the discharged biomass 2 can also be diluted with the filtrate before the discharged biomass 2 is treated with the enzyme, for example, if the discharged biomass 2 is diluted by the filtrate upstream of the neutralization unit 9. After being treated in the neutralization unit 9, the biomass (now with a pH value of around the suitable pH interval for enzyme stage, for example around pH 5, alternatively between 4.75 and 5.25 or 4.7 and 5.3) can be fed to the hydrolysis reactor unit 10 for being exposed to an enzymatic hydrolysis process as described above. Alternatively, the biomass 2 can be diluted with filtrate in the downstream part of reactor 8 before being discharged.

While the invention has been illustrated and described in detail in the drawings and the foregoing description, such illustration and description are to be considered illustrative and exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims the term "comprising" does not exclude other elements, and the indefinite article "a" or "an" does not exclude a plurality. The mere fact that certain measures are recited in mutually different dependent

The invention claimed is:

1. A method for treating biomass, the method comprising:
   impregnating the biomass with a reactant in an impregnation reactor unit prior to feeding the impregnated biomass to a pressurized prehydrolysis reactor unit;
   feeding the impregnated biomass to the pressurized prehydrolysis reactor unit by means of a feeding system, wherein by means of the feeding system the impregnated biomass is compressed, and wherein a filtrate is squeezed out of the impregnated biomass by means of the feeding system;
   separating the filtrate from the impregnated biomass;
   thermally treating the impregnated biomass in the pressurized prehydrolysis reactor unit to form a thermally treated biomass;
   diluting the thermally treated biomass with the filtrate after thermal treatment but before being discharged from the pressurized prehydrolysis reactor unit to form a diluted biomass, wherein a pH value of the diluted biomass is adjusted to between 4.7 and 5.3;
   discharging the diluted biomass from the pressurized prehydrolysis reactor unit to form a discharged biomass;
   and
   treating the discharged biomass with an enzyme.

2. The method of claim 1, wherein the diluted biomass is discharged from the pressurized prehydrolysis reactor through a steam explosion.

3. The method of claim 1, wherein the reactant is water, acid or a catalyst.

4. The method of claim 1, wherein the biomass is fed to the impregnation reactor unit by means of a first plug screw of the feeding system, wherein the impregnation reactor unit is partly filled with the reactant, and wherein the filtrate is squeezed out of the biomass by means of the first plug screw while the biomass is fed to the impregnation reactor unit by means of the first plug screw.

5. The method of claim 1, wherein the filtrate is squeezed out of the impregnated biomass by means of a second plug screw of the feeding system while the impregnated biomass is fed to the pressurized prehydrolysis reactor unit by means of the second plug screw.

6. A method for treating biomass, the method comprising:
   impregnating the biomass with a reactant in an impregnation reactor unit prior to feeding the impregnated biomass to a pressurized prehydrolysis reactor unit;
   feeding the impregnated biomass to the pressurized prehydrolysis reactor unit by means of a feeding system, wherein by means of the feeding system the impregnated biomass is compressed, and wherein a filtrate is squeezed out of the impregnated biomass by means of the feeding system;
   separating the filtrate from the impregnated biomass;
   thermally treating the impregnated biomass in the pressurized prehydrolysis reactor unit to form a thermally treated biomass;
   discharging the thermally treated biomass from the pressurized prehydrolysis reactor unit to form a discharged biomass;
   diluting the discharged biomass with the filtrate to form a diluted biomass, wherein a pH value of the diluted biomass is adjusted to between 4.7 and 5.3; and
   enzymatically treating the discharged biomass during the diluting step and/or enzymatically treating the diluted biomass.

* * * * *